(12) United States Patent
Stauffer

(10) Patent No.: US 8,114,917 B1
(45) Date of Patent: Feb. 14, 2012

(54) ETHANOL SYNTHESIS

(76) Inventor: John E. Stauffer, Greenwich, CT (US)

( * ) Notice: Subject to any disclaimer, the term of this patent is extended or adjusted under 35 U.S.C. 154(b) by 0 days.

(21) Appl. No.: 13/023,895

(22) Filed: Feb. 9, 2011

(51) Int. Cl.
*C07C 27/00* (2006.01)
(52) U.S. Cl. .......................... 518/714; 518/700; 518/713
(58) Field of Classification Search .................. 518/700, 518/713, 714
See application file for complete search history.

(56) References Cited

U.S. PATENT DOCUMENTS 4,618,628 A * 10/1986 Head et al. .................... 518/700

OTHER PUBLICATIONS

G. A. Olah et al., "Beyond Oil and Gas: The Methanol Economy", Wiley-VCH Verlag GmbH & Co. pp. 174-175, Feb. 2006, Weinheim, Germany.

* cited by examiner

*Primary Examiner* — Jafar Parsa
(74) *Attorney, Agent, or Firm* — Young Basile Hanlon & MacFarlane, PC

(57) ABSTRACT

A process is disclosed for the production of ethanol whereby synthesis gas is reacted to produce ethanol and carbon dioxide in the presence of a compound catalyst at a temperature in the range of 250° C. to 350° C. and a pressure of 1 atm. to 20 atm.

1 Claim, 2 Drawing Sheets

ETHANOL SYNTHESIS

FIELD OF THE INVENTION

The present invention relates to a process for the manufacture of ethanol from synthesis gas. In the process, a gas mixture of carbon monoxide and hydrogen is passed over a compound catalyst at an elevated temperature to produce ethanol and carbon dioxide.

BACKGROUND OF THE INVENTION

There are two principal routes for the commercial production of ethanol. One procedure starts with ethylene and by means of catalytic hydration produces ethanol. The other methods depend on fermentation using primarily corn or sugar cane as the raw materials. The economics of these processes depends largely on such factors as the cost of petroleum, commodity prices, and government subsidies. As a result, there is a degree of uncertainty in the supply of ethanol in world markets.

Looking to find new sources of ethanol, industry has spent considerable effort on developing novel processes. One approach is based on synthesis gas as a feedstock. The chemistry depends on the conversion of two mols of carbon monoxide and four mols of hydrogen to produce one mol of ethanol and one mol of water.

Success in this research has so far been elusive. In spite of recent optimism, the final outcome remains in doubt.

SUMMARY OF THE INVENTION

A process is provided for the production of ethanol from synthesis gas. In the preferred process, three mols of carbon monoxide are reacted with three mols of hydrogen to produce one mol of ethanol and one mol of carbon dioxide.

The reaction is conducted in the gas phase over a compound catalyst comprising an intimate mixture of three separate catalysts. The catalysts are copper chromite, copper zinc oxide, and promoted activated carbon. The reaction temperature is in the range of about 250° C. to about 350° C. and the pressure is about 1 atm. to about 20 atm.

A tubular reactor is preferred for carrying out the continuous process. Means are provided for removing the heat of reaction. The effluent stream from the reactor is cooled and the ethanol product is condensed. Byproduct carbon dioxide is recovered while any unreacted synthesis gas is recycled.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying photographs, the latter being briefly described hereinafter.

BRIEF SUMMARY OF THE DRAWINGS

The description herein makes reference to the accompanying drawings wherein like reference numerals refer to like parts throughout the several views and wherein.

DETAILED DESCRIPTION OF THE PREFERRED EMBODIMENT

The process described herein comprises four chemical reactions that occur simultaneously in the same reactor. Thus, a product of one reaction is a reactant in another reaction or is one of the final products of the process. These four reactions can be illustrated by the following equations.

$$CO + 2H_2 \rightarrow CH_3OH \tag{1}$$

$$2CH_3OH + CO \rightarrow CH_3COOCH_3 + H_2O \tag{2}$$

$$CH_3COOCH_3 + 2H_2 \rightarrow C_2H_5OH + CH_3OH \tag{3}$$

$$H_2O + CO \rightarrow H_2 + CO_2 \tag{4}$$

When the above equations are combined by adding them together, the following expression is obtained.

$$3CO + 3H_2 \rightarrow C_2H_5OH + CO_2 \tag{5}$$

Equation (5) represents the overall reaction of the process. It shows that three mols of carbon monoxide (CO) react with three mols of hydrogen ($H_2$) to produce one mol of ethanol ($C_2H_5OH$) and one mol of carbon dioxide ($CO_2$).

The reaction shown by equation (1) represents the synthesis of methanol ($CH_3OH$). The conditions for this reaction are critical. It requires Cu/ZnO catalyst and is carried out at 250° C. to 300° C. under 100 atm. pressure.

The preparation of acetic acid from methanol and carbon monoxide by carbonylation is shown in equation (2) only in this case, methyl acetate ($CH_3COOCH_3$) is formed in preference to acetic acid. The withdrawal of water ($H_2O$) favors the formation of acetate. This reaction is catalyzed by activated carbon, which may be promoted with titania, alumina or silica. The reaction takes place in the range of about 300° C. to about 350° C. and at about 700 atm, pressure.

Although the direct reduction of organic acids is not practical, their esters react readily with hydrogen to form the corresponding alcohol. This reaction is given in equation (3). Thus, methyl acetate is converted to ethanol and methanol. The catalyst for the reaction is copper chromite. The reaction temperature is over 200° C. and elevated pressures are used.

Equation (4) represents the water gas shift reaction. By this means, water is reacted with carbon monoxide to produce hydrogen and carbon dioxide. An active zinc oxide-copper oxide catalyst permits the operation at temperatures below 315° C. and at low pressures.

The conditions necessary for the individual reactions shown by equations (1)-(4) dictate the requirements for the overall reaction of equation (5). Accordingly, the catalyst is made up of an intimate mixture of pellets or granules with the following compositions: copper zinc oxide, promoted activated carbon, and copper chromite. This mixture is placed in the reactor and serves as the catalyst bed for the heterogeneous reaction. The optimum reaction temperature is in the range of about 250° C. to about 350° C. The pressure, however, will deviate from the values shown for most of the individual reactions. It will depend instead on equilibrium conditions as determined by thermodynamics.

Figure 1:
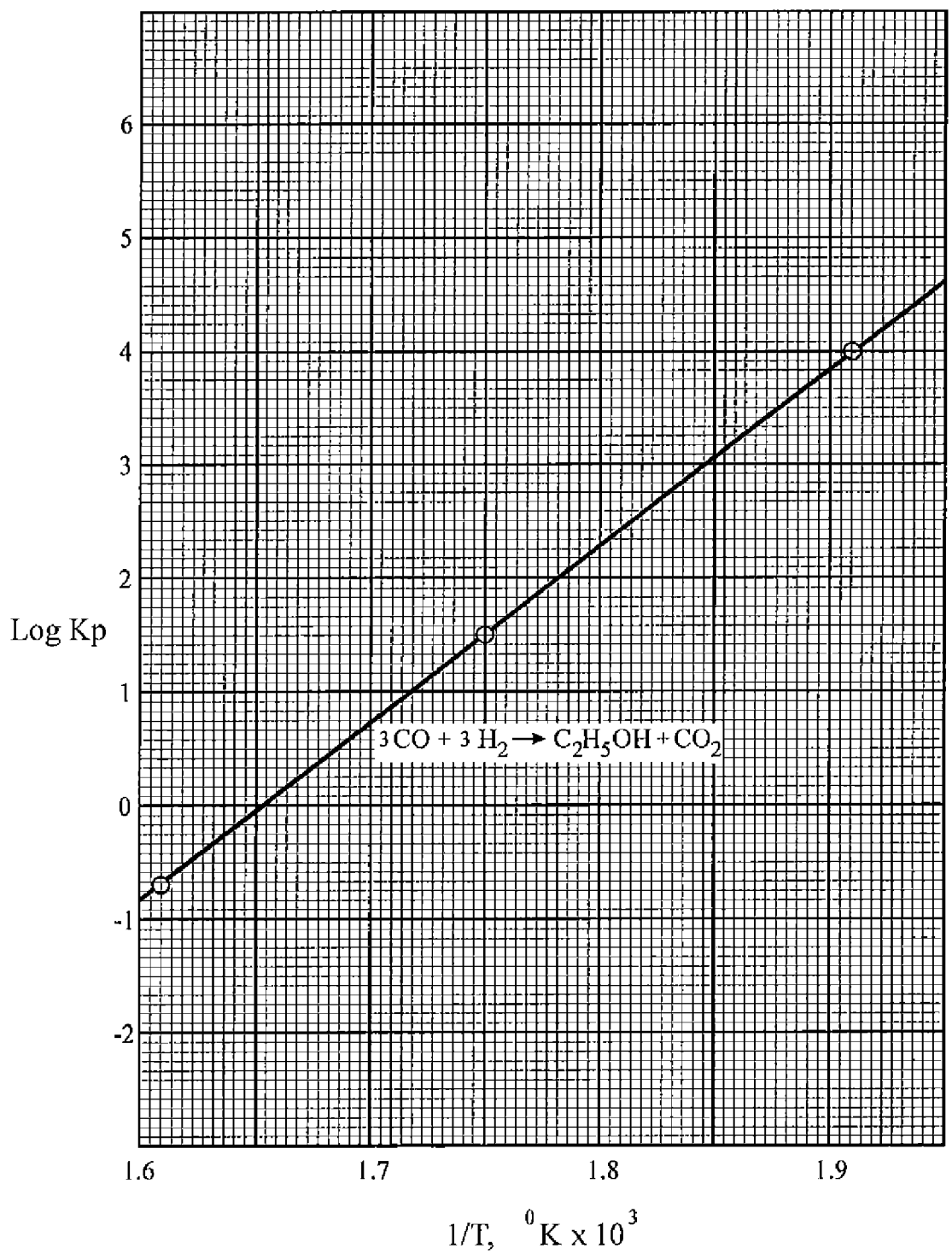
FIG. 1 is a graph showing the equilibrium conversion at given temperatures for the overall reaction, namely, the reaction of carbon monoxide with hydrogen to give ethanol and carbon dioxide.

Equilibrium constants were calculated for the reaction of equation (5) from the heat and free energy of formation for the reactants and products. The results indicate that log Kp equals +3.98 at 250° C., 1.50 at 300° C., and −0.67 at 350° C. These data are plotted on the graph shown in FIG. 1. Equilibrium conditions are quite favorable, showing that the conversion of synthesis gas to ethanol and carbon dioxide proceeds quite smoothly.

Notwithstanding favorable equilibrium data, there is an advantage in using elevated pressures in the process. Because six mols of reactants are converted to two mols of product, applied pressure will increase the conversion. Balancing this advantage with the cost of compressing the gases, the recommended pressure is in the range of about 1 atm. to 20 atm. A further advantage of using moderate pressure is that the size of the equipment can be reduced.

Figure 2:
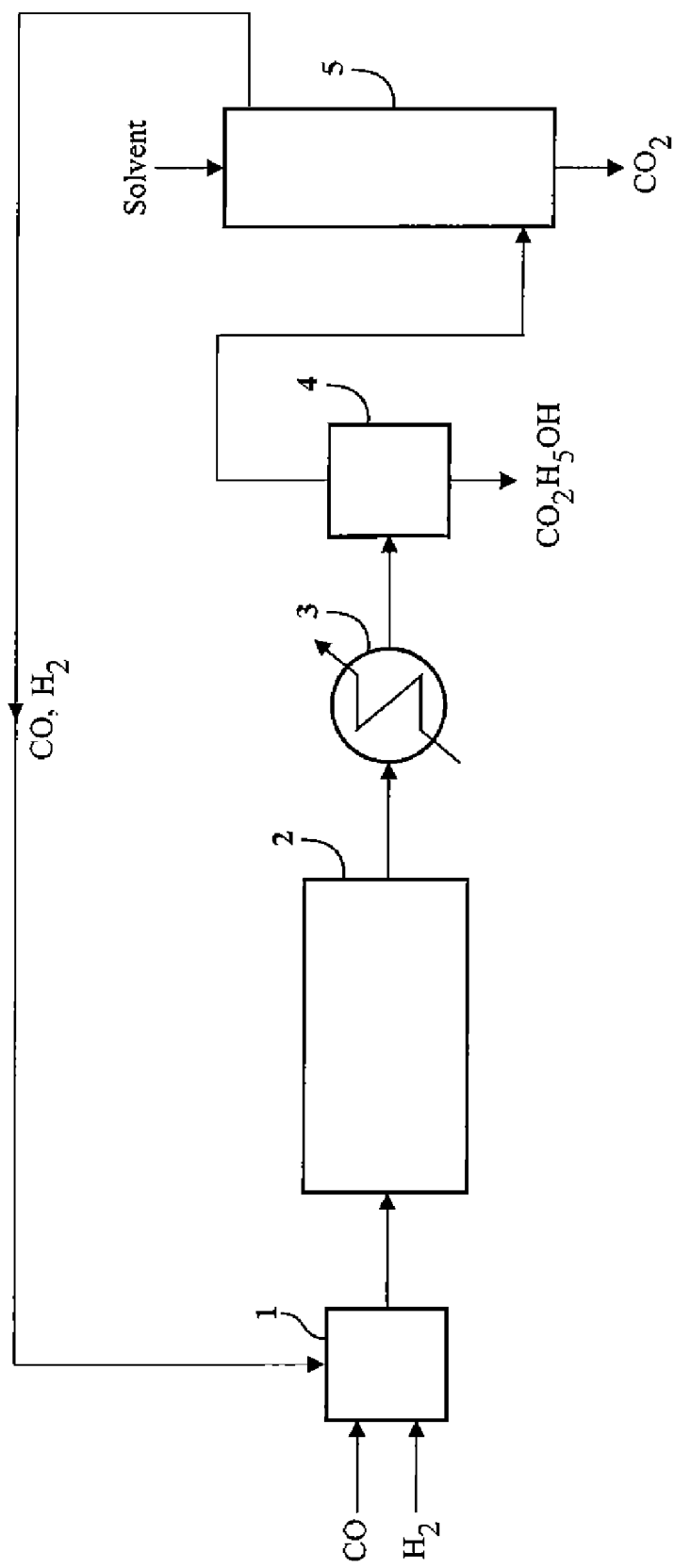
FIG. 2 is a schematic flow sheet of the process, identifying the major pieces of equipment that are numbered for convenient reference.

A better understanding of the process of the present invention can be obtained by referring to the block diagram in FIG. 2. In this drawing, preheater 1 brings the reactants up to the reaction temperature. Reactor 2 may be of a shell and tube design. Heat exchanger 3 cools the exit gases and condenses the product ethanol, which is recovered in separator 4. And finally, carbon dioxide is removed from the gas stream by scrubber 5 before unreacted synthesis gas is recycled to the preheater.

The advantages of the present invention are numerous. High yields of product are obtained in a process designed to operate under mild conditions. Utility costs are minimized by the relatively high conversions. Absolute alcohol is produced directly. Most important, much of the technology is proven, thus ensuring a dependable and robust process.

What is claimed is:

1. A process for the manufacture of ethanol from synthesis gas consisting of the gas phase reaction of carbon monoxide with hydrogen to produce ethanol and carbon dioxide; said reaction being conducted in the presence of a catalyst comprising a mixture of copper chromite catalyst, copper zinc oxide catalyst, and promoted activated carbon catalyst; and operated at a reaction temperature in the range of about 250° C. to 350° C. and a pressure in the range of about 1 atm. to 20 atm.

* * * * *